United States Patent [19]
Arakawa et al.

[11] Patent Number: 5,266,372
[45] Date of Patent: * Nov. 30, 1993

[54] FIXING TAPE

[75] Inventors: Masaaki Arakawa; Teiji Sakashita; Kazumasa Sibata; Katsumi Hori; Makoto Takahashi; Naomitu Tanaka, all of Osaka, Japan

[73] Assignee: Nitto Denko Corporation, Osaka, Japan

[*] Notice: The portion of the term of this patent subsequent to May 7, 2010 has been disclaimed.

[21] Appl. No.: 879,346

[22] Filed: May 7, 1992

Related U.S. Application Data

[63] Continuation of Ser. No. 424,635, Oct. 20, 1989, Pat. No. 5,134,012.

[30] Foreign Application Priority Data

Apr. 24, 1989 [JP] Japan .................................. 1-47996

[51] Int. Cl.[5] .............................................. C09J 7/02
[52] U.S. Cl. ..................................... 428/40; 428/152; 428/354
[58] Field of Search ............... 428/343, 352, 354, 152, 428/173, 40; 604/389, 390

[56] References Cited

U.S. PATENT DOCUMENTS

| | | | |
|---|---|---|---|
| 4,168,196 | 9/1979 | Nemeth | 428/40 |
| 4,237,889 | 12/1980 | Gobran | 428/343 |
| 4,393,115 | 7/1983 | Yoshii | 428/343 |
| 4,568,344 | 2/1986 | Suzuki | 604/389 |
| 4,769,024 | 9/1988 | Pike | 604/390 |
| 4,808,474 | 2/1989 | Sipinen | 428/343 |
| 5,134,012 | 7/1992 | Arakawa | 428/152 |

FOREIGN PATENT DOCUMENTS

| | | | |
|---|---|---|---|
| 0246009 | 11/1987 | European Pat. Off. | |
| 2830536 | 1/1980 | Fed. Rep. of Germany | |
| 0112006 | 6/1984 | Japan | 604/389 |
| 9002540 | 3/1990 | PCT Int'l Appl. | 604/389 |

*Primary Examiner*—Jenna L. Davis
*Attorney, Agent, or Firm*—Sughrue, Mion, Zinn, Macpeak & Seas

[57] ABSTRACT

A fixing tape is disclosed, which comprises a plastics film having a two- or three-layer construction comprising a plastics film layer and a polymer blend layer formed on at least one side of the plastics film layer, one side of the polymer blend layer facing away from the plastics film layer being a satin surface.

4 Claims, 2 Drawing Sheets

FIXING TAPE

This is a continuation of application Ser. No. 07/424,635 filed Oct. 20, 1989 now U.S. Pat. No. 5,134,012.

FIELD OF THE INVENTION

This invention relates to a fixing tape for fixing a paper diaper, a medical instrument or the like to the human body.

BACKGROUND OF THE INVENTION

The applicant of the present invention has earlier proposed a film used as a substrate for a tape for fixing a diaper to the human body described in JP-A-63-112704. (The term "JP-A" as used here in means an unexamined published Japanese patent application). This conventional tape substrate is made of a blend of one or more of an ethylene-vinyl acetate copolymer, a polyethylene and an ethylene-propylene copolymer with a polypropylene, the polypropylene content being 5 to 75 wt %. This conventional diaper-fixing tape, used in direct contact with the skin of the baby or infant, has been proposed in view of the handle or drape and the softness in an attempt to prevent the baby skin from being subjected to a rash, redness and a laceration. However, this conventional tape substrate has been found not entirely satisfactory in that it is a little rigid. This difficulty arises out of the fact that the processability encountered when producing the tape has been taken into account.

Tests of this conventional diaper-fixing tape by monitors have indicated that a rash and a laceration have not appeared on the skin, but the redness on the skin has not been improved sufficiently.

SUMMARY OF THE INVENTION

With the above deficiencies of the prior art in view, it is an object of the present invention to provide a fixing tape best suited for fixing a diaper or other medical instrument to the skin of the human body which tape has a good drape or handle, and is so soft as not to irritate or damage the skin, and can be easily held between the fingers, and looks soft and gives a high-quality impression.

The above and other objects and effects of the present invention will be more apparent from the following description.

According to the present invention, there is provided a fixing tape comprising a plastics film having a two- or three-layer construction comprising a plastics film layer and a polymer blend layer formed on at least one side of the plastics film layer, one side of the polymer blend layer facing away from the plastics film layer being a satin surface.

An adhesive layer may be provided on at least one surface of the plastics film by applying an adhesive agent. On the portion of the surface of the plastics film where the adhesive layer is not provided, a back face treating layer may be provided for facilitating the release of an adhesive layer of another fixing tape and the prevention of rubbing or sticking of other materials to be in contact with the fixing tape.

BRIEF DESCRIPTION OF THE DRAWINGS

FIGS. 1(*b*) to 1(*d*) are cross-sectional views of fixing tapes provided in accordance with another embodiments of the present invention.

DETAILED DESCRIPTION OF THE INVENTION

The inventors of the present invention have made an extensive study in an attempt to obtain a diaper-fixing tape which is gentler or softer to the skin, and found that the fixing tape of the above construction has increased softness and handle or drape Since the tape has the satin surface, the tape can be easily held by the fingers because of a high coefficient of friction of the satin surface, and thereby facilitating the fixing of the diaper to the skin. Further, the satin surface does not have a gloss, which gives a high-quality impression.

If the tape substrate is merely made solely of a film of polyethylene or polypropylene, or a film of an ethylenevinyl acetate copolymer or an ethylene-propylene copolymer, which have a good handle or drape, the following disadvantages are encountered:

(1) Since the surface of the film is smooth, a release agent is liable to be removed by friction.

(2) Most of such films has a poor reactivity with a silicone used as a back face treating agent.

(3) The film is too soft and has no nerve.

(4) The film made of polypropylene is liable to be torn.

The fixing tape of the present invention has the satin surface, and therefore the removal of a back face treating agent is prevented, and also the reactivity with silicone is improved, (Of course, the satin surface must be free from an antioxidant and a metal which restrict the reaction with silicone). Further, the plastics film is of a two- or three-layer laminated construction, that is the upper layer or the upper and lower layers are laminated with the polymer blend layers having the satin surface. With this construction, the fixing tape of the present invention is sufficiently soft but has an increased nerve, and cannot be torn easily. Therefore, the fixing tape is best suited for fixing a diaper or other medical instrument to the human body, since the fixing tape can be freely flexed following the motion of the human body.

If the satin surface like those in the present invention is intended to be formed after fabricating the plastics film, the use of sandblast or a textured roll is required. This is undesirable since it increases the number of process steps and hence increases the cost. However, in the present invention, the laminated film comprising the satinized polymer blend layer and the plastic film layer of a good handle or drape can be obtained by a simultaneous molding method. Therefore, the fixing tape of the present invention can be produced at low costs.

The fixing tapes of the present invention will now be described with reference to the drawings.

Figure 1:
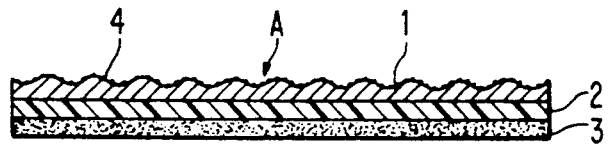
FIGS. 1(*a*1) and 1(*a*2) each is a cross-sectional view of a fixing tape provided in accordance with one embodiment of the present invention.
Figure 1:
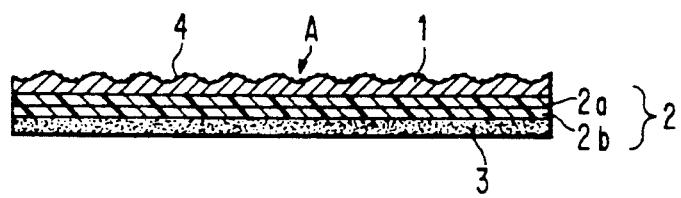

FIGS. 1(*a*1) and 1(*a*2) each shows a fixing tape A according to the present invention. The fixing tape comprises a plastics film layer 2, and a polymer blend layer 1 formed on one side of the plastics film layer 2. An adhesive layer 3 is provided on the other side of the plastics film layer 2. In the embodiment in FIG. 1(a2), the plastics film layer 2 is composed of two layers 2a and 2b. The polymer blend layer 1 has an outer surface which is satinized. A release agent layer or back face treating layer 4 is optionally formed on the satinized surface of the polymer blend layer 1.

Figure 1B:
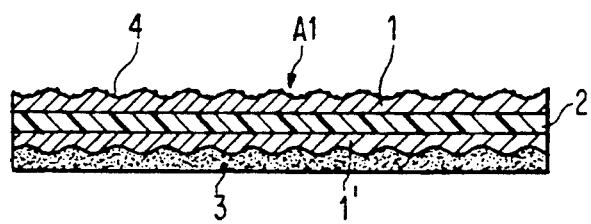
Figure 1C:
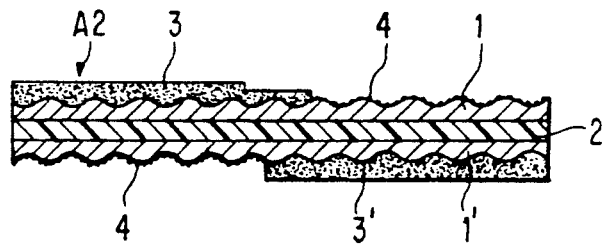
Figure 1D:
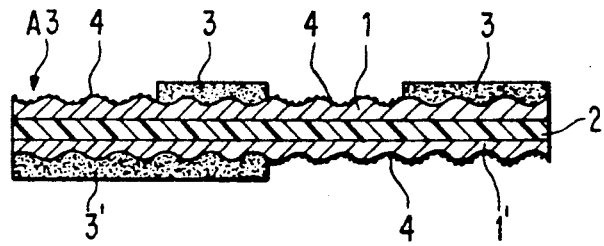

FIGS. 1(b) to 1(d) show modified fixing tapes A1 to A3 according to another embodiments of the present invention.

In the fixing tape A1 of FIG. 1(b), a pair of polymer blend layers 1 and 1' are formed respectively on the opposite sides of the plastics film layer 2, each polymer blend layer having an outer satinized surface as described above in the preceding embodiment. The adhesive layer 3 is formed on the satin surface of the lower polymer blend layer 1'. A release agent layer or a back face treating layer 4 is formed on the satin surface of the upper polymer blend layer 1.

In the fixing tape A2 of FIG. 1(c), the pair of polymer blend layers 1 and 1' are formed respectively on the opposite sides of the plastics film layer 2, as described above for the fixing tape A1 of FIG. 1(b). A pair of upper and lower adhesive layers 3 and 3' of a smaller width are formed respectively on the satin surfaces of the upper and lower polymer blend layers 1 and 1'. More specifically, the upper adhesive layer 3 is formed on a generally half width of the satin surface of the upper polymer blend layer 1. The lower adhesive layer 3' is formed on a generally half width of the satin surface of the lower polymer blend layer 1'. The upper and lower adhesive layers 3 and 3' are disposed generally asymmetrically with respect to the longitudinal axis or centerline of the fixing tape A2. In the illustrated embodiment, each of the upper and lower adhesive layers 3 and 3 has a width greater than a half of the width of the fixing tape A2. The portions of the satin surfaces of the polymer blend layers 1 and 1' where the adhesive layers 3 and 3' are not provided are provided with the release agent layer or the back face treating layer 4.

In the fixing tape A3 of FIG. 1(d), the pair of polymer blend layers 1 and 1' are formed respectively on the opposite sides of the plastics film layer 2, as described above for the fixing tape A1 of FIG. 1(b). An adhesive layer 3' is formed on a generally half of the satin surface of the lower polymer blend layer 1'. Adhesive layers 3 and release agent layers or back face treating layers 4 are formed alternately and patternwise on the satin surface of the upper polymer blend layer 1. Alternatively, both the satin surfaces of the polymer blend layers 1 and 1' may be provided with the adhesive layers 3 and 3' and the release agent layer or the back face treating layers 4 formed alternately and patternwise.

Figure 2:
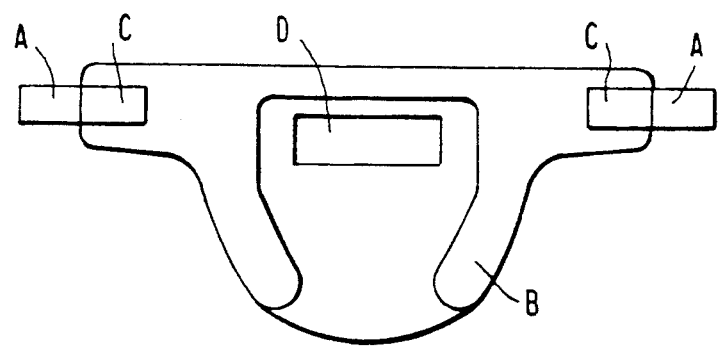
FIG. 2 is a front-elevational view of a diaper using the fixing tapes of the present invention.

FIG. 2 shows a diaper B to which fastener tapes comprising the fixing tapes of the present invention are attached. Reference characters C and D each denotes a fastening tape. The fixing tapes A and A1 of FIGS. 1(a1), 1(a2) and 1(b) can be used as the fastening tapes C and D.

The plastics film layer 2 of the fixing tape of each of the above embodiments has a good handle or drape. The plastics film layer 2 can be made of any one or mixture of a polyethylene, a polypropylene, an ethylene-vinyl acetate copolymer and an ethylene-propylene copolymer. The plastics film layer 2 preferably has a width direction compression strength of 200 g/mm$^2$ or less, and more preferably from 40 to 100 g/mm$^2$. By using the plastics film layer having a width direction compression strength within the above range, a fixing tape having appropriate softness and nerve can be obtained.

The "width direction compression strength" used herein is determined by the following manner: the plastics film sample (65 mm $\times$ 25 mm) is made a loop (diameter: 20 mm) by looping in the longitudinal direction; the loop is placed on a plate and pressed in the width direction at 23° C., 65% RH at a rate of 10 mm/min; the maximum pressing force at which the loop starts to collapse is divided by the thickness of the plastics film sample to obtain the width direction compression strength.

Preferred examples of the material for the plastics film layer 2 include an ethylene/vinyl acetate copolymer having a vinyl acetate content of 4% or more, a very low density polyethylene (VLDPE), a low density polyethylene (LDPE), a linear low density polyethylene (L-LDPE), a ethylene/propylene copolymer having a ratio of ethylene/propylene of from 9/1 to 1/9, and a chlorinated polypropylene, as well as a mixture of a polypropylene with at least one of a polyethylene, an ethylene/propylene copolymer and an ethylene/vinyl acetate copolymer having a ratio of the polypropylene to the other resins of from 0/10 to 9/1, more preferably from 4/6 to 6/4.

The polymer blend layer 1, which is formed on at least one side of the plastics film layer 2 and has the satin surface, can be made of a polymer blend comprising at least two resins selected from the group consisting of an ethylene-vinyl acetate copolymer, an ethylene-propylene copolymer and a polyethylene. It is preferred that the polymer blend layer 1 be made of a polymer blend composed of at least one of a polyethylene and an ethylene/propylene copolymer with a polypropylene, the polypropylene content being 5 to 95 wt %, more preferably 5 to 75 wt %. In this case, a low-density polyethylene film is preferably used as the plastics film layer 2. A mixture of a polypropylene and a polyethylene having a polypropylene content of 75 wt % is most preferred for the polymer blend layer.

The thickness of the plastics film composed of the polymer blend layer 1 and the plastics film layer 2 is usually from 1 $\mu$m to 1 mm, but is not limited to such thickness. The thickness of the polymer blend layer 1 is preferably from 3 to 5 $\mu$m, and the thickness of the plastics film layer 2 is preferably from 30 to 200 $\mu$m.

Such a plastic film is preferably obtained by a simultaneous extrusion molding method using a T-die.

An adhesive agent of which the adhesive layer 3 is made is not particularly limited, and the adhesive layer 3 may be made of a known adhesive agent such as an acrylic type adhesive agent, a rubber type adhesive agent and a styrene type adhesive agent. The thickness of the adhesive layer 3 is usually from 5 to 500 $\mu$m, but is not limited to such thickness.

The back face treating layer can be formed by using any conventional methods and materials, and is preferably formed by coating a silicone or a long-chain alkyl release coating agent.

The present invention will now be illustrated by referring to the following Examples and Comparative Examples, but the present invention is not construed as being limited thereto.

EXAMPLES

Various films having a two- or three-layer construction were prepared using various polymers shown in Table 1. The films of a two- or three-layer construction were formed by a simultaneous extrusion molding method using a T-die, the temperature of the die being 180° C. Then, a styrene-type adhesive agent was applied to one side of each of the thus prepared films to form an adhesive layer having a thickness of 50 μm, thereby providing fixing tapes. In the samples of Example 1, 2 and 4, the adhesive layer is formed on the intermediate layer; and the sample of Example 3, the adhesive layer is formed on the lower layer. Various tests, which include the handle or drape (softness), the nerve and the reactivity with silicone as a back face treating agent, of the thus obtained fixing tapes were carried out, and the results of the tests and total evaluation are shown in Table 1.

the silicone from the film. If the ink formed cissings, the silicone was remained and the reactivity was evaluated as good (A). If the ink was uniformly coated, the silicone was removed by rubbing and the reactivity was evaluated as poor (C).

4. Overall evaluation: The suitability of the samples for a fixing tape for fixing a diaper or a medical instrument to the human body was evaluated in view of the results of the tests 1 to 3 above. The evaluation was made in terms of excellent (A), good (B), and poor (C).

As is clear from the above Table 1, it has been recognized that the fixing tapes of the present invention used as a fastener tape for a diaper is hardly irritating to the skin, and has sufficient softness and nerve, so that the

TABLE 1

|  | Example | | | | Comparative example | | |
| --- | --- | --- | --- | --- | --- | --- | --- |
|  | 1 | 2 | 3 | 4 | 1 | 2 | 3 |
| Polymer composition | | | | | | | |
| Upper layer | PE/PP 30/70 | PE/PP 70/30 | PE/E-P/PP 30/10/60 | EVA/PP 30/70 | — | — | — |
| Intermediate layer | L-LDPE | PP | L-LDPE | EVA | EVA | L-LDPE | PP |
| Lower layer | — | — | PE/E-P/PP 30/10/60 | — | — | — | — |
| Layer thickness (μm) | | | | | | | |
| Upper layer | 20 | 20 | 10 | 50 | — | — | — |
| Intermediate layer | 80 | 40 | 130 | 150 | 200 | 100 | 60 |
| Lower layer | — | — | 10 | — | — | — | — |
| Total thickness | 100 | 60 | 150 | 200 | 200 | 100 | 60 |
| Test results | | | | | | | |
| Handle or drape (softness) | 10/10 | 9/10 | 8/10 | 9/10 | 9/10 | 10/10 | 0/10 |
| Nerve (mm) | 2 | 8 | 0–1 | 3–5 | 20–25 | 15–20 | 6–8 |
| Reactivity with silicone | A | A | A | A | C | C | C |
| Overall evaluation | A | B | A | A | C | C | C |

Note:
PE: Polyethylene (V-141; manufactured by Nippon Oil Company, Ltd.)
PP: Polypropylene (J-350G; manufactured by Nippon Oil Company, Ltd.)
E-P: Ethylene-propylene copolymer (Tafmer P-0680; manufactured by Mitsubishi Oil Co., Ltd.)
EVA: Ethylene-vinyl acetate copolymer (H-616-3; manufactured by Mitsubishi Oil Co., Ltd.)
L-LDPE: Low-pressure low-density polyethylene (Ultzex 3010F; manufactured by Mitsubishi Oil Co., Ltd.)
LDPE: Low-density polyethylene (V-141N; manufactured by Nippon Oil Company, Ltd.)

The evaluation in the above Table 1 was conducted in the following manner:

1. Handle or drape (softness): Organoleptic tests by ten monitors were conducted to determine the feeling through the eyes and the feeling through contact with the skin. The results were indicated in terms of the number of the monitors who determined the sample having good handle or drape per the total number of the monitors.

2. Nerve: Each fixing tape was adhesively bonded to a polyester plate of which back face was treated by a long-chain alkane at 23° C., 65% RH and pressed twice with a 2 kg roller, and after 30 minutes, the fixing tape was peeled at a rate of 300 mm/min. The tape was placed on a flat plate such that the concave of the tape was made upward. The nerve was determined by checking the degree of curling in terms of the perpendicular distance between the plate and the edge of the tape.

3. Reactivity with silicone: Silicone (X-62-1148; manufactured by Shin-etsu Silicone Co., Ltd.) was coated on the upper layer (Examples 1 to 4) or the intermediate layer (Comparative Examples 1 to 3) of each substrate in an amount of 0.5 g/m², and then the substrate was heated for 30 seconds at 100° C. Subsequently, the silicone coated layer was rubbed once with the finger to check the degree of curing of the silicone coating. Thereafter, the silicone-coated film was further rubbed five times with the finger, and then a lipophilic ink was coated on the film to see how the lipophilic ink was coated thereon, thus judging the degree of removal of fixing tape material is very practical and a good processability.

Therefore, the fixing tapes of the present invention can be suitably used not only as a diaper fixing tape but also as a tape for fixing a medical instrument to the human body.

While the invention has been described in detail and with reference to specific examples thereof, it will be apparent to one skilled in the art that various changes and modifications can be made therein without departing from the spirit and scope thereof.

What is claimed is:

1. A fixing tape comprising:
   a plastic film layer;
   a polymer blend layer formed directly on one side of said plastic film layer, where the side of said polymer blend layer facing away from said plastic film layer has a satin surface; and
   an adhesive layer provided on at least one portion of the side of said plastic film layer facing away from said polymer blend layer.

2. The fixing tape as claimed in claim 1, wherein said plastic film layer comprises two or three layers.

3. The fixing tape as claimed in claim 1, further comprising a second adhesive layer provided on at least one portion of said satin surface of said polymer blend layer.

4. The fixing tape as claimed in claim 1, further comprising a releasing agent layer formed on the satin surface of said polymer blend layer.

* * * * *